(12) United States Patent
Crawford et al.

(10) Patent No.: US 7,101,351 B2
(45) Date of Patent: Sep. 5, 2006

(54) SAFETY DEVICE FOR A SYRINGE

(75) Inventors: Jamie Crawford, New York, NY (US); Frank Francavilla, Branchville, NJ (US); Roger Groskopf, Saddle Brook, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 436 days.

(21) Appl. No.: 10/700,009

(22) Filed: Nov. 3, 2003

(65) Prior Publication Data

US 2005/0096599 A1     May 5, 2005

(51) Int. Cl.
*A61M 5/00* (2006.01)
(52) U.S. Cl. ...................................... 604/110
(58) Field of Classification Search ............... 604/110, 604/192, 198, 263, 164.05
See application file for complete search history.

(56) References Cited

U.S. PATENT DOCUMENTS

| | | | |
|---|---|---|---|
| 4,573,976 A | 3/1986 | Sampson |
| 4,631,057 A | 12/1986 | Mitchell |
| 4,737,144 A | 4/1988 | Choksi |
| 4,747,831 A | 5/1988 | Kulli |
| 4,795,432 A | 1/1989 | Karczmer |
| 4,813,940 A | 3/1989 | Parry |
| 4,985,021 A | 1/1991 | Straw |
| 4,998,920 A | 3/1991 | Johnson |
| 5,026,356 A | 6/1991 | Smith |
| 5,053,018 A | 10/1991 | Talonn |
| 5,061,251 A | 10/1991 | Juhasz |
| 5,151,088 A | 9/1992 | Allison |
| 5,156,599 A | 10/1992 | Ranford |
| 5,163,918 A | 11/1992 | Righi |
| 5,193,552 A | 3/1993 | Columbus |
| 5,197,953 A | 3/1993 | Colonna |
| 5,201,708 A | 4/1993 | Martin |
| 5,217,437 A | 6/1993 | Talonn |
| 5,242,420 A | 9/1993 | Martin |
| 5,246,427 A | 9/1993 | Sturman |
| 5,273,541 A | 12/1993 | Malenchek |
| 5,300,040 A | 4/1994 | Martin |
| 5,304,149 A | 4/1994 | Morigi |
| 5,308,332 A | 5/1994 | Dillard, III |
| 5,312,372 A | 5/1994 | DeHarde et al. |
| 5,336,176 A | 8/1994 | Yoon |
| 5,342,309 A | 8/1994 | Hausser |
| 5,342,320 A | 8/1994 | Cameron |
| 5,370,628 A | 12/1994 | Allison |

(Continued)

FOREIGN PATENT DOCUMENTS

EP     0 307 367 A1     6/1992

(Continued)

*Primary Examiner*—Sharon Kennedy
(74) *Attorney, Agent, or Firm*—David M. Fortunato

(57) ABSTRACT

A medical device including a syringe assembly and a shield system for delivering medicament to a patient. The syringe assembly includes a barrel defining a medicament reservoir, a needle cannula coupled to the barrel and in fluid communication with the reservoir, a plunger having a stopper positioned in the reservoir and a thumb pad for moving the plunger in the reservoir. The shield system has a first shield coupled to a forward end of the barrel, and a second shield movable from a first position disposed from the needle cannula tip to a second position covering the needle cannula tip. An urging member controlled by a retaining device urges the second shield to the second position upon movement of the stopper to a position which releases the retaining device.

41 Claims, 10 Drawing Sheets

U.S. PATENT DOCUMENTS

| | | |
|---|---|---|
| 5,385,555 A | 1/1995 | Hausser |
| 5,389,085 A | 2/1995 | D'Alessio |
| 5,417,660 A | 5/1995 | Martin |
| 5,562,626 A | 10/1996 | Sanpietro |
| 5,651,774 A | 7/1997 | Taranto |
| 5,658,254 A | 8/1997 | Reichenbach |
| 5,681,292 A | 10/1997 | Tober |
| 5,713,871 A | 2/1998 | Stock |
| 5,735,823 A | 4/1998 | Berger |
| 5,769,822 A | 6/1998 | McGary |
| 5,800,395 A | 9/1998 | Botich |
| 5,800,403 A | 9/1998 | Pressly |
| 5,882,342 A | 3/1999 | Cooper |
| 6,017,329 A | 1/2000 | Hake |
| 6,077,253 A | 6/2000 | Cosme |
| 6,162,197 A | 12/2000 | Mohammad |
| 6,228,054 B1 | 5/2001 | Dysarz |
| 6,319,233 B1 | 11/2001 | Jansen |
| 6,432,087 B1 | 8/2002 | Hoeck et al. |
| 6,432,088 B1 | 8/2002 | Huang et al. |
| 6,440,104 B1 | 8/2002 | Newby et al. |
| 6,443,929 B1 | 9/2002 | Kuracina |
| 6,458,101 B1 | 10/2002 | Hu |
| 6,458,105 B1 | 10/2002 | Rippstein et al. |
| 6,461,333 B1 | 10/2002 | Frezza |
| 6,461,362 B1 | 10/2002 | Halseth |
| 6,475,194 B1 | 11/2002 | Domici, Jr. |
| 6,478,780 B1 | 11/2002 | Shields |
| 6,494,863 B1 | 12/2002 | Shaw |
| 6,511,460 B1 | 1/2003 | Arnissolle |
| 6,514,229 B1 | 2/2003 | Huang |
| 6,527,742 B1 | 3/2003 | Malenchek |
| 6,530,903 B1 | 3/2003 | Wang |
| 6,547,762 B1 | 4/2003 | Botich |
| 6,558,357 B1 | 5/2003 | Hoeck |
| 6,565,540 B1 | 5/2003 | Perouse |
| 6,569,115 B1 | 5/2003 | Barker |
| 6,569,124 B1 | 5/2003 | Perouse |
| 6,589,209 B1 | 7/2003 | Dysarz |
| 6,595,954 B1 | 7/2003 | Luther |
| 6,605,073 B1 | 8/2003 | Pressly |
| 6,817,989 B1 * | 11/2004 | Svendsen et al. ........... 604/192 |
| 2002/0065488 A1 | 5/2002 | Suzuki et al. |
| 2002/0193737 A1 | 12/2002 | Popovsky |
| 2002/0193746 A1 | 12/2002 | Chevallier |
| 2002/0193747 A1 | 12/2002 | Denolly |
| 2003/0023205 A1 | 1/2003 | Botich |
| 2003/0028171 A1 | 2/2003 | DeHarade |
| 2003/0036730 A1 | 2/2003 | Von Teichert |
| 2003/0050601 A1 | 3/2003 | Righi |
| 2003/0050607 A1 | 3/2003 | Gaagnieux |
| 2003/0078546 A1 | 4/2003 | Jensen |
| 2003/0083627 A1 | 5/2003 | Chen |
| 2003/0114799 A1 | 6/2003 | Cheikh |
| 2003/0144630 A1 | 7/2003 | Chang |
| 2003/0149403 A1 | 8/2003 | Barker |
| 2003/0149404 A1 | 8/2003 | Lehmann |
| 2004/0044312 A1 | 3/2004 | Svendsen et al. |
| 2004/0236281 A1 | 11/2004 | Popovsky |

FOREIGN PATENT DOCUMENTS

| | | |
|---|---|---|
| EP | 0 680 767 A1 | 11/1995 |
| EP | 0 864 335 A2 | 9/1996 |
| EP | 0 740 942 A1 | 11/1996 |
| EP | 0 966 983 A1 | 12/1999 |
| EP | 1 066 848 A2 | 6/2000 |
| EP | 1 258 263 A1 | 11/2002 |
| EP | 1 260 242 A1 | 11/2002 |
| EP | 0 901 391 B1 | 1/2003 |
| EP | 0 963 213 B1 | 1/2003 |
| EP | 1 273 316 A1 | 1/2003 |
| EP | 1 281 410 A1 | 2/2003 |
| EP | 0 916 354 B1 | 3/2003 |
| EP | 1 287 842 A1 | 3/2003 |
| EP | 1 291 029 A1 | 3/2003 |
| EP | 1 291 030 A1 | 3/2003 |
| EP | 1 317 938 A1 | 6/2003 |
| EP | 0 984 804 B1 | 7/2003 |
| EP | 1 329 234 A2 | 7/2003 |
| EP | 0 941 134 B1 | 8/2003 |
| EP | 1 205 173 A2 | 9/2003 |
| EP | 1 205 173 A3 | 9/2003 |
| EP | 0 734 738 B1 | 10/2003 |
| EP | 1 049 503 B1 | 10/2003 |
| EP | 1 472 980 A1 | 4/2004 |
| FR | 2 830 764 A1 | 4/2003 |
| FR | 2 830 765 A1 | 4/2003 |
| GB | 2 282 069 A | 3/1995 |
| JP | 2001193714 | 12/2002 |
| WO | WO 01/41841 A2 | 6/2001 |
| WO | WO 01/41841 A3 | 6/2001 |
| WO | WO 01/60435 A1 | 8/2001 |
| WO | WO 01/85238 A2 | 11/2001 |
| WO | WO 02/089878 A1 | 11/2002 |
| WO | WO 02/098480 A2 | 12/2002 |
| WO | WO 02/098494 A2 | 12/2002 |
| WO | WO 02/098494 A3 | 12/2002 |
| WO | WO 03/000322 A1 | 1/2003 |
| WO | WO 03/000323 A1 | 1/2003 |
| WO | WO 03/011378 A1 | 2/2003 |
| WO | WO 03/015852 A1 | 2/2003 |
| WO | WO 03/022335 A2 | 3/2003 |
| WO | WO 03/033059 A1 | 4/2003 |
| WO | WO 03/033060 A1 | 4/2003 |
| WO | WO 03/041766 A2 | 5/2003 |
| WO | WO 03/045476 A1 | 6/2003 |
| WO | WO 03/045480 A1 | 6/2003 |
| WO | WO 03/045481 A1 | 6/2003 |
| WO | WO 03/063934 A1 | 8/2003 |
| WO | WO 03/068297 A1 | 8/2003 |
| WO | WO 03/068298 A1 | 8/2003 |

\* cited by examiner

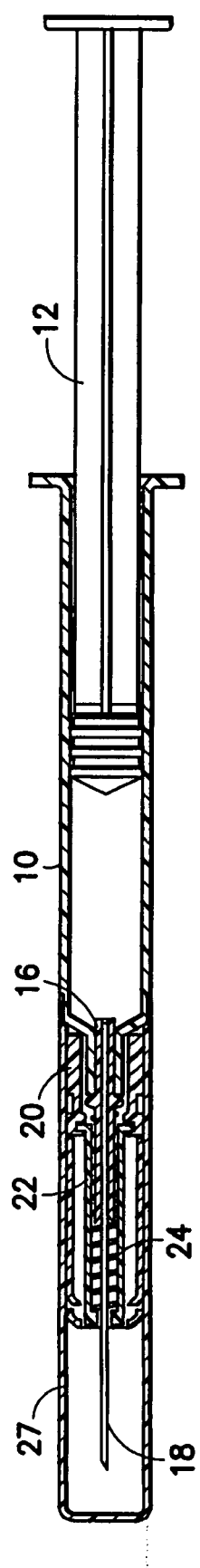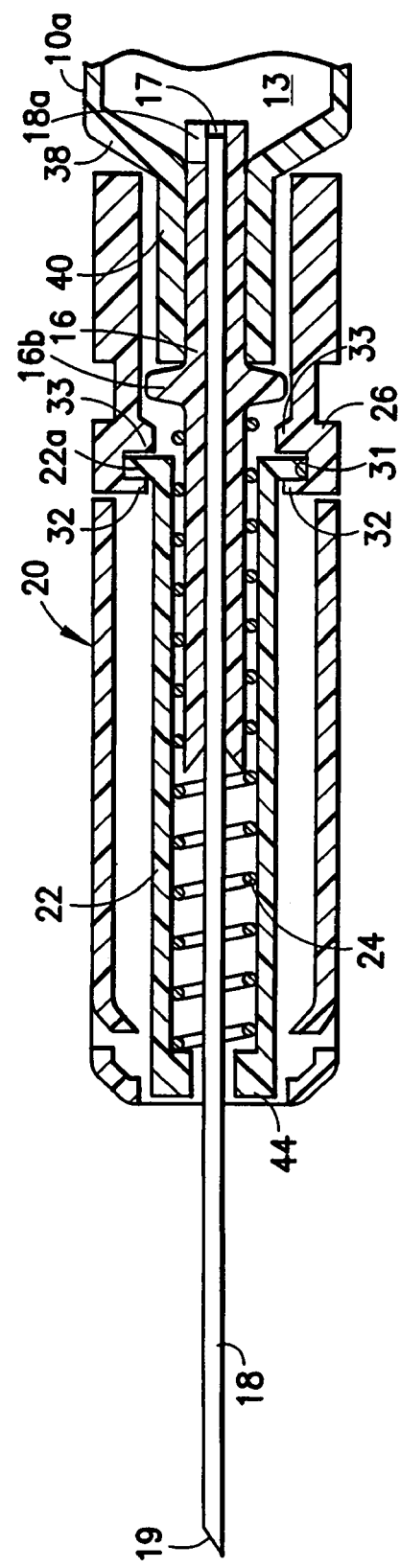
FIG.2
FIG.3

SAFETY DEVICE FOR A SYRINGE

BACKGROUND OF THE INVENTION

1. Field of the Invention

The present invention relates to a medical device for delivering a dose of medicament by injection and having a shield system for preventing accidental needle sticks after use. More particularly, the present invention is directed to a syringe assembly including a safety shield system.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled medicament. Such syringes typically include a cylindrical hollow barrel which may be formed of a glass or plastic material and which includes the medicament. One end of the barrel is fitted with a fixed or removable hollow needle, and the other end of the barrel receives a plunger having a stopper which is slidable with respect to the barrel for delivery of the medicament to the hollow needle, i.e., to urge the medicament toward and out of the needle. A syringe assembly, which typically includes the above-described components, is usually stored with a removable needle cover which protects the needle from damage during storage and handling. Prior to use, the needle cover is removed to expose the needle.

To prevent a syringe user and, in particular, a health care professional from inadvertent sticks by the needle after use of the syringe on a patient, the syringe assembly may incorporate a safety shield which forms a guard to cover the needle after use. Certain attributes to be considered in such syringe assemblies are that the shield should be intuitive and easy to use, should preferably provide consistent and reliable shield deployment, and should be operable with one hand. Other attributes are that such syringe assemblies require no change in current medicament delivery techniques, allow for dose adjustment, are autoclavable, and allow for the inspection of contents before and after activation of the shield. Moreover, the use of the shield must not detrimentally affect processing and loading of the syringe at the pharmaceutical company, the assembly (i.e., syringe assembly and safety shield) must be easy to manufacture, must prevent accidental activation, and must limit the possibility of incurring cosmetic or structural damages.

SUMMARY OF THE INVENTION

The present invention relates to a syringe incorporating a safety shield for covering the needle after administration of the dosage of medicament in the syringe. The safety shield is automatically activated upon full delivery of the medicament dosage in the syringe. As used herein, the term "medicament" is intended to refer to any drug substance, vaccine, or other liquid substance that is injected into a patient.

The object is met by a medical device for delivery of a dosage of medicament to a patient which includes a syringe assembly and a shield system. The syringe assembly includes a cylindrical barrel having a forward end and a rear end and a reservoir defined therebetween and within which a medicament may be held and from which the medicament may be expelled. The syringe assembly also includes a cannula or needle cannula (those terms being used interchangeably herein) provided at the forward end of the barrel and having a forward tip and a rear end in fluid communication with the reservoir for delivery of the medicament to the patient. The syringe assembly further includes a plunger rod having a stopper arranged at one end and a thumb pad or thumb press area arranged at the other end, the thumb pad being operable for receiving medicament delivery pressure for pressing the stopper of the plunger rod into the barrel and causing the stopper to move within the barrel to cause delivery of the medicament. The terms "thumb pad" and "thumb press area" designate a region coupled to or otherwise formed on an end of the plunger for receiving force applied to the plunger in an intended manner.

The shield system comprises a first shield connectable proximate the front end of the barrel, a second shield movable from a first position to a second position. The shield system also includes an urging member urging the second shield toward the second position, a retaining device for holding the second shield in the first position, and a release mechanism for releasing the retaining device after the stopper has been fully inserted into the barrel, wherein the forward tip of the needle cannula is at least partially exposed when the second shield is in the first position, and the forward tip of the needle cannula is covered by the second shield when the second shield is in the second position.

The second shield of the shield system is inserted telescopically in the first shield when the second shield is in the first position. Furthermore, the end of the second shield facing the barrel has a flange which interacts with the retaining device for holding the second shield in the first position. The retaining device may include a flexible arm arranged on the first shield having a retaining element for interaction with the flange. The release mechanism includes a tubular element arranged on the needle cannula and which is sealingly inserted with the needle cannula in an opening at the front of the barrel. The tubular element extends into the barrel such that the stopper contacts the tubular element at a contact position before the stopper is fully inserted in the barrel. When the stopper is moved passed the position of contact with the tubular element, the tubular element is pushed by the stopper as the stopper moves from the contact position to the fully inserted position. The tubular element is arranged to force the flexible arm radially outward when the tubular element is moved by the stopper to release the second shield.

The tubular element of the release mechanism includes a tubular portion and a flange portion arranged between two longitudinal ends of the tubular portion. The tubular portion is molded from a rigid material for supporting the needle cannula and the flange portion is molded from a flexible material having a flexibility sufficient to provide a seal at the front of the barrel. The flange portion may interact with the retaining device to release the second shield.

The urging member, which may, for example, comprise a spring, is arranged between the tubular element and the second shield. More specifically, the urging member is arranged between the flange portion of the tubular element and the second shield.

The first shield may comprise a lip at a front end thereof for retaining the flange of the second shield at the front end of the first shield when the second shield is released. The first shield may further comprise a locking device for locking the second shield in the second position. The locking device may include a flexible arm which allows the flange to pass the flexible arm as the second shield moves toward the second position and prevents the second shield from moving back toward the first position from the second position.

The second shield may comprise an annular bump between first and second ends thereof and the retaining device may comprise a lip arranged at a front end of the first shield which interacts with the annular bump. In this embodiment, the release mechanism may comprise a tubular element arranged on the needle cannula with a hub portion facing the barrel. The hub portion contacts the stopper at a contact position before the stopper reaches a fully inserted position. The tubular element and hub are then pushed by the stopper when the stopper moves to the fully inserted position in the barrel. The tubular element moves the second shield such that the annular bump is forced passed the lip to release the second shield when the stopper is moved to the fully inserted position.

The barrel of the syringe may comprise a cylindrical barrel portion for holding the medicament, and a front portion having a small cylinder and a transition portion between the small cylinder and the cylindrical barrel portion. The release mechanism includes a tubular element arranged on the needle cannula and is sealingly inserted with the needle cannula in an opening defined by the small cylinder. The first shield is connected on an outer surface of the small cylinder. The barrel of the syringe may be made from a plastic material or a glass material as is known in the art. Alternatively, the cylindrical barrel portion may be made from a glass material and the front portion may be made from a plastic material.

The object of the invention is also met by a shield system for connection to a syringe for preventing inadvertent needle sticks after use of the syringe. The shield system comprises a first shield connectable proximate a forward end of the syringe, a second shield movable from a first position to a second position, an urging member urging the second shield toward the second position, a retaining device for holding the second shield in the first position, and a release mechanism for releasing the retaining device from the first position.

The present invention allows one-hand operation and requires no change in current medicament delivery techniques. Since the entire shield assembly is arranged in front of the medicament holding portion of the syringe, the present invention allows dose adjustment, allows inspection of contents after activation of the shield, and the drug and scale on the syringe are visible to the end user. Activation of the shield does not interfere with administration of the dose because the shield is activated after the dose has been fully delivered.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 2 is a cross-sectional side view of the medical device of FIG. 1 prior to use;

FIG. 3 is an enlarged view of a shield system in the state shown in FIG. 2;

DETAILED DESCRIPTION OF THE PREFERRED EMBODIMENTS

Figure 1:
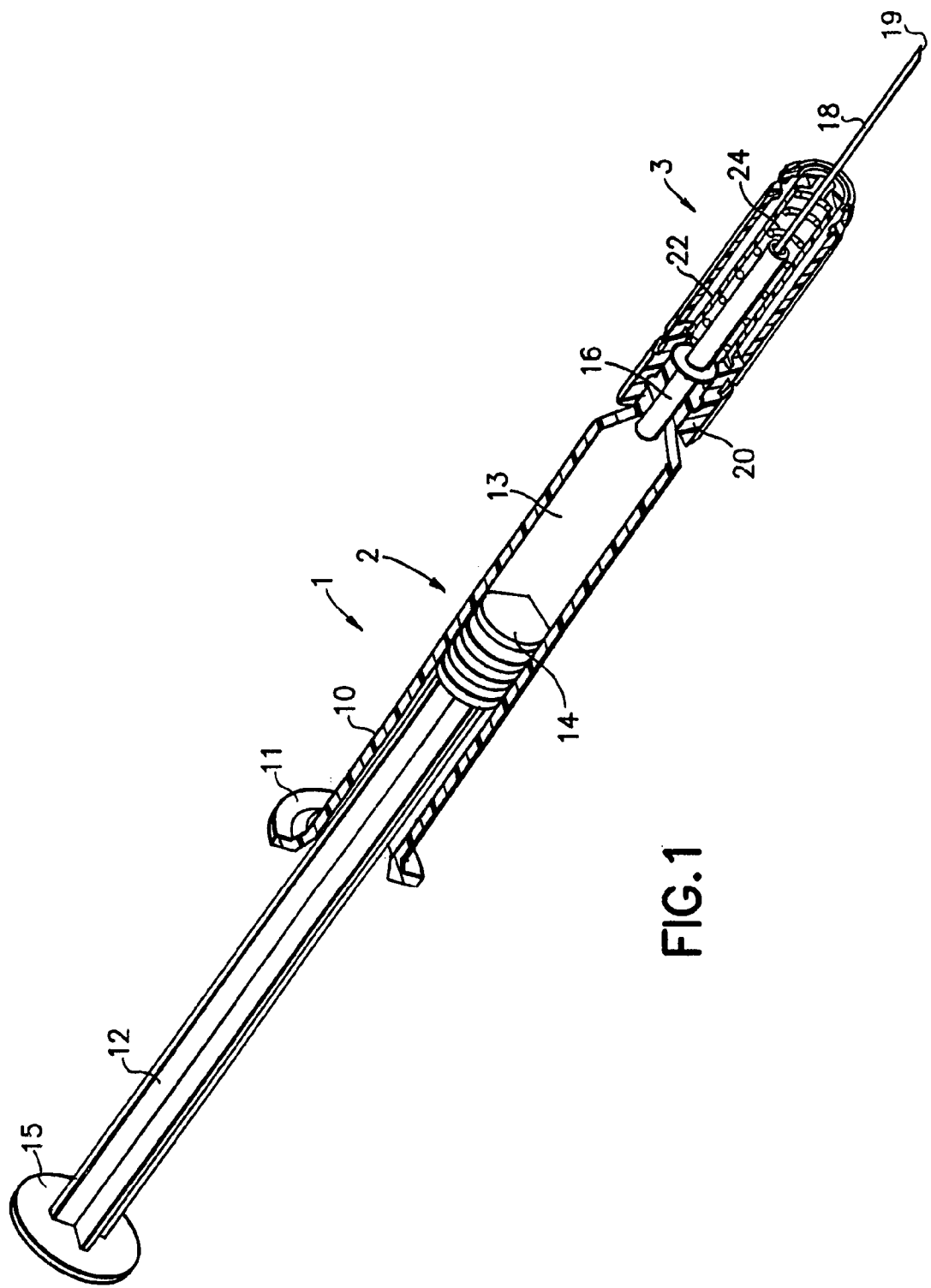
FIG. 1 is a partial cross-sectional perspective view of the components of a medical device having a syringe assembly and a shield system according to the present invention.

FIGS. 1 and 2 show a medical device 1 for delivery of a medicament into a patient constructed in accordance with the present invention. The medical device 1 includes a syringe assembly 2 which can be prefilled with the medicament to be delivered, and a shield system 3 connected to the syringe assembly 2.

The syringe assembly 2 comprises a generally cylindrical barrel 10 defining a reservoir 13 within which the medicament may be contained. The syringe assembly 2 further comprises and a needle cannula 18 having a forward tip 19 and a rear end 17 which is in fluid communication with the reservoir 13 and which is connected at a front end of the barrel 10 by a needle pusher 16 which will be explained in more detail below. The needle cannula 18 may comprise any sharp or blunt tubular device which is used for delivering a medicament to a patient. The barrel 10 may be made of any glass or plastic material suitable for holding a medicament. The syringe assembly 2 further comprises a plunger rod 12 having a first end inserted in the barrel 10. A stopper or piston 14 arranged on the first end of the plunger rod 12 is longitudinally movable with the plunger rod 12 within the barrel 10. A second end of the plunger rod 28 includes a thumb press area or thumb pad 15 which receives pressure from the user's thumb for pressing the piston 14 into the barrel 10 and for moving the piston 14 in and through the reservoir 13 for delivering the medicament.

Figure 12:
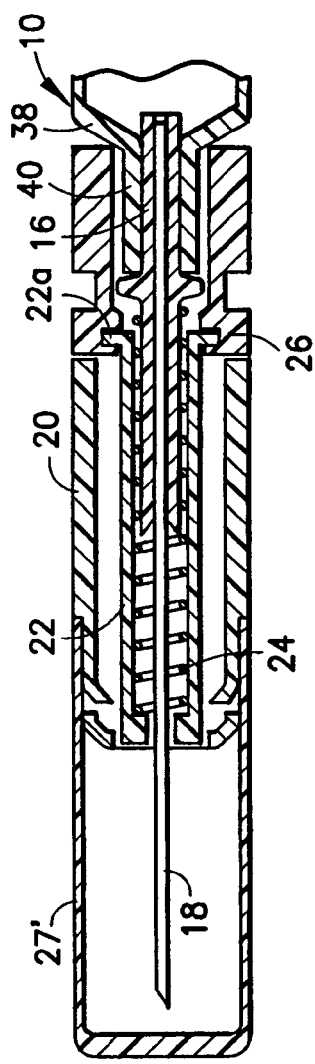
FIG. 12 is an enlarged cross-sectional view of a shield system showing an alternative needle shield.

The rear end of the barrel 10 includes a flange 11 which functions as a finger rest to facilitate the delivery of the medicament. Instead of flange 11, other finger rest configurations may be formed, such as two opposing projections or other flange configurations arranged at different areas along the barrel. The shield system 3 surrounds the external portion of the needle cannula 18 on the front end of the barrel 10. To protect the needle cannula and to protect users from being stuck by the needle prior to its intended use, a removable needle shield 27 (see FIG. 2) is connected to the front of the barrel 10 covering both the needle 18 and the shield system 3. As an alternative, a removable needle shield 27' may be designed to connect to the front end of the shield system 3 as shown in FIG. 12 so as to only cover the needle cannula 18.

Figure 4:
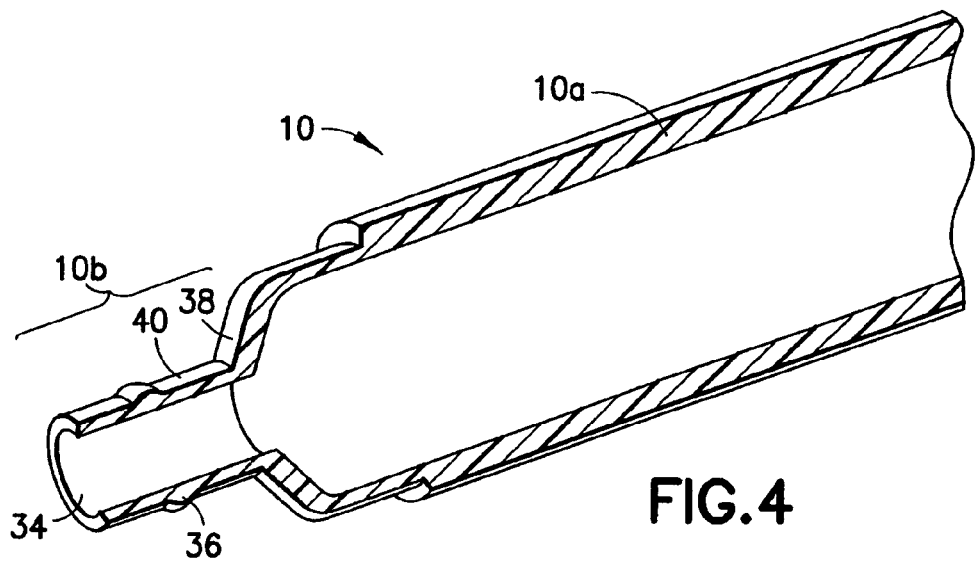
FIG. 4 is a cross-sectional perspective view of a barrel of the syringe assembly of the medical device of FIG. 1.

As shown in FIG. 4, the barrel 10 comprises a cylindrical section 10a and a front section 10b. The front section 10b includes a small cylinder 40 and a transition section 38 which connects the small cylinder 40 to the cylindrical section 10a. As stated above, the barrel 10 may comprise glass or plastic. Alternatively, the cylindrical section 10a may comprise glass and the front section 10b may comprise plastic. This allows the small cylinder 40 to be formed, such as by molding, with a circumferential bump or collar 36. The function of the collar 36 is described below.

Figure 5:
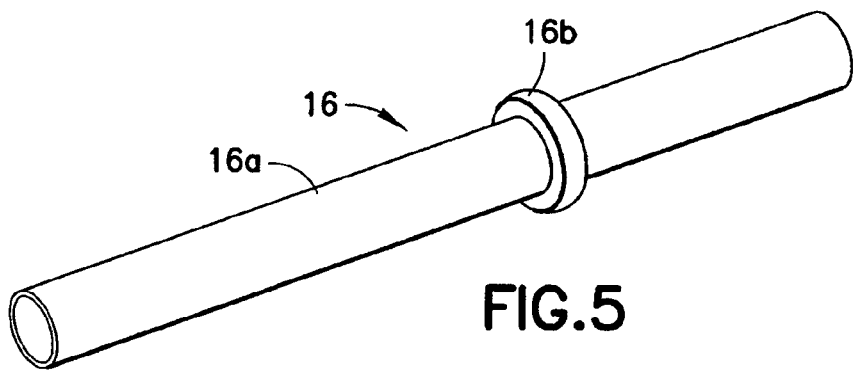
FIG. 5 is a perspective view of a needle pusher part of the medical device of FIG. 1.

As shown in FIG. 5, the needle pusher 16 includes a tubular piece 16a which fits through an opening 34 defined through the small cylinder 40 of the front section 10b. The needle pusher 16 also includes a flange portion 16b arranged on the tubular piece 16a and which provides a seal at the tip of the small cylinder 40 during use. The needle pusher 16 is preferably molded from two different materials. The tubular piece 16a is formed of a resilient moldable material, such as plastic, which provides the necessary rigidity for supporting the needle 18. The flange portion 16b is formed of a flexible material, such as rubber, having sufficient elasticity to function as a gasket between the tubular piece 16a and the barrel 10.

Figure 6:
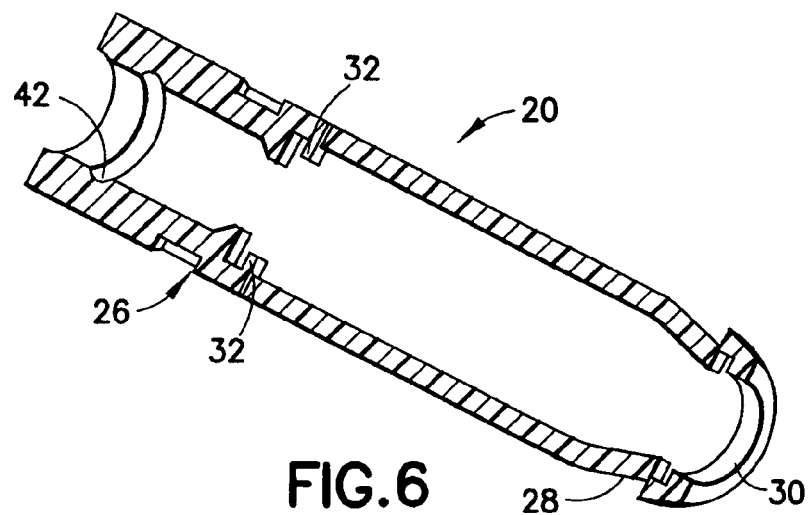
FIG. 6 is a cross-sectional perspective view of a first shield of a medical device according to the present invention.

Referring to FIGS. 1, 2, and 6, the shield system 3 includes a first shield 20 which is cylindrical and connected to barrel 10 by a snap fit. Specifically, the first shield 20 is received on the small cylinder 40 so that the annular bump 36 on the small cylinder 40 fits into an annular recess 42 defined on an inner surface of the first shield, thereby holding the first shield 20 onto the barrel 10. Alternatively, or in addition to the snap-fit connection, the first shield 20 may be permanently connected to the barrel 10 using an adhesive or other more permanent connection. The connection may also be, by way of non-limiting example, made by one of press fitting, spin welding, heat stake, or threading.

Figure 13:
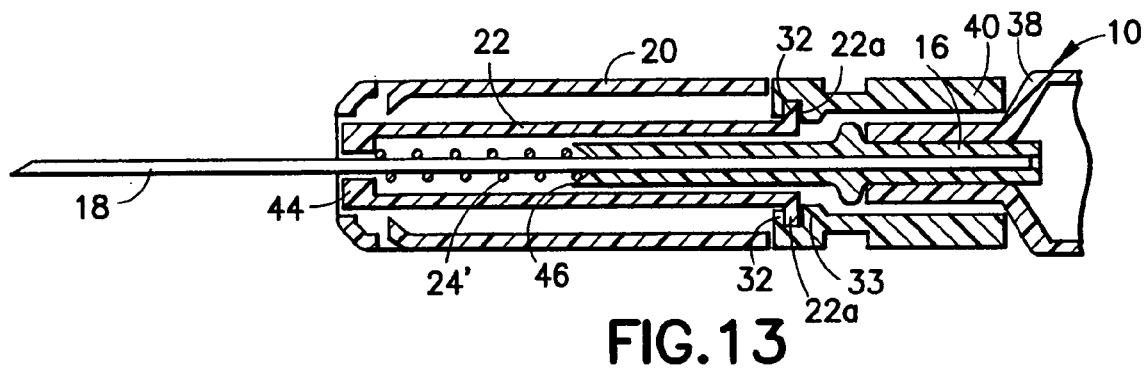
FIG. 13 is an enlarged cross-sectional view of a shield system showing an alternative configuration of an urging element.

Referring also to FIG. 3, a second shield 22 is arranged within the first shield 20. The second shield 22 has a radially outwardly extending flange 22a on an end of the second shield 22 and in a direction of the first shield 20. An urging member 24, such as, for example, a spring, is arranged between the flange portion 16b of the needle pusher 16 and a front wall 44 of the second shield 22. The urging member 24 may be arranged anywhere between the second shield 22 and the needle pusher 16 or between the first shield 20 and the second shield 22. For example, FIG. 13 shows the urging member 24 arranged between the front wall 44 of the second shield 22 and a front face 46 of the needle pusher 16. As shown in FIG. 3, the portion of first shield 20 proximate transition section 38 has a flexible collar 26 which may, alternatively, be configured as flexible arms configured to have a radial channel 31 formed between a retaining member 32 and a shoulder 33 for seating about the flange 22a. An edge of the shoulder 33 which faces the gasket 16b is angled to facilitate movement of the gasket 16b over the shoulder 33 as explained below. The seating of the flange 22a in channel 31 prevents the second shield 22 from moving forward toward the end of needle cannula 18 under the urgency of the spring 24, which is maintained in a "charged" state before deployment of the second shield 22.

Figure 7:
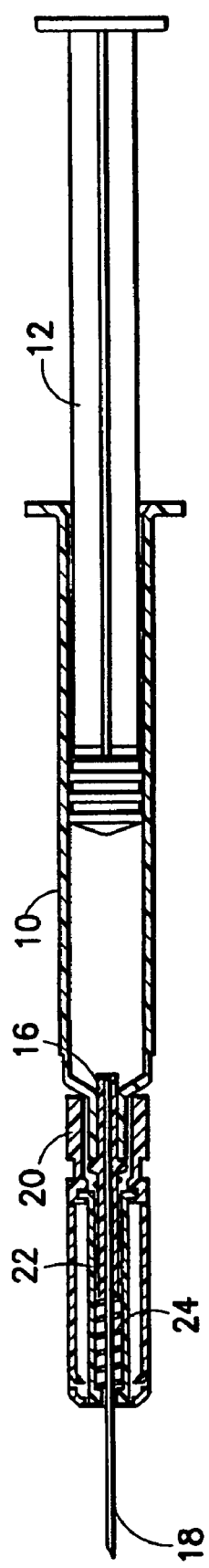
FIG. 7 is a cross-sectional side view of the medical device of FIG. 1 ready for use.
Figure 8:
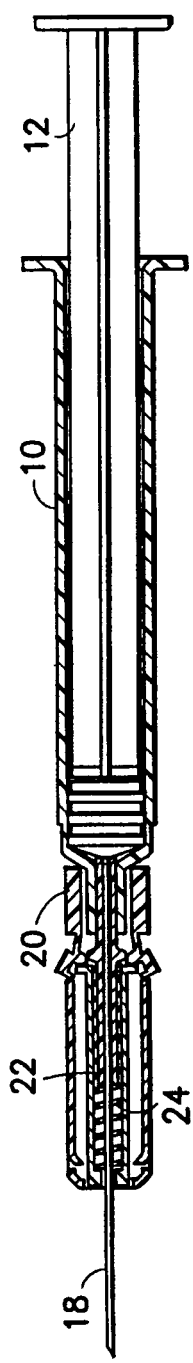
FIG. 8 is a cross-sectional side view of the medical device of FIG. 1 with the plunger rod and stopper at a position to release the second shield.
Figure 9:
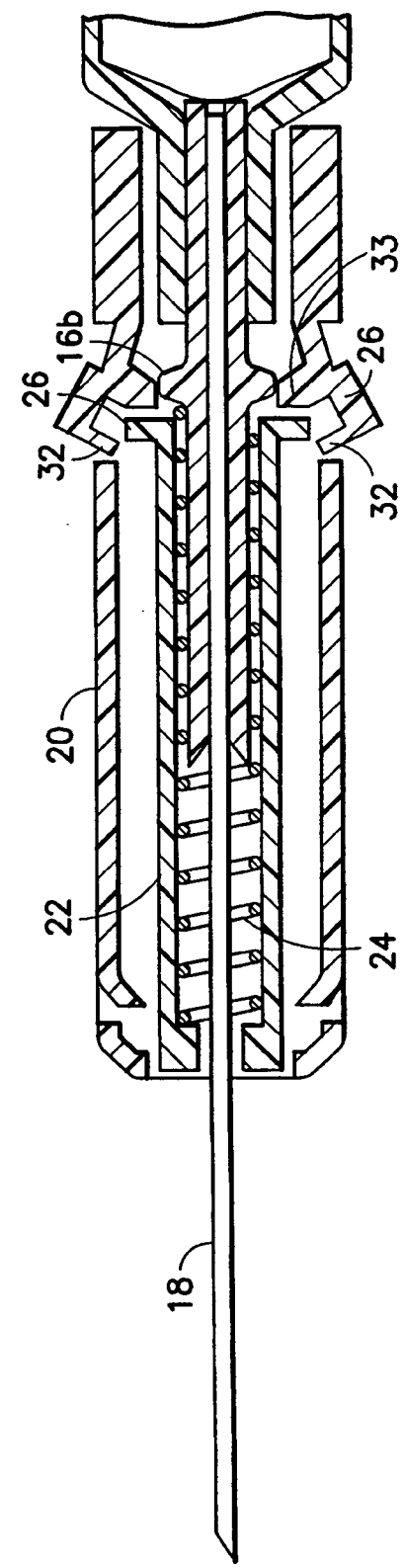
FIG. 9 is an enlarged view of the shield system in the state shown in FIG. 8.
Figure 10:
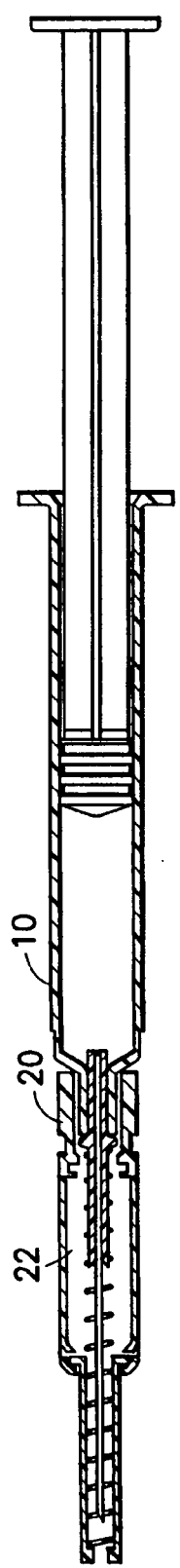
FIG. 10 is a cross-sectional side view of the medical device of FIG. 1 depicting the second shield positioned over the needle cannula.
Figure 11:
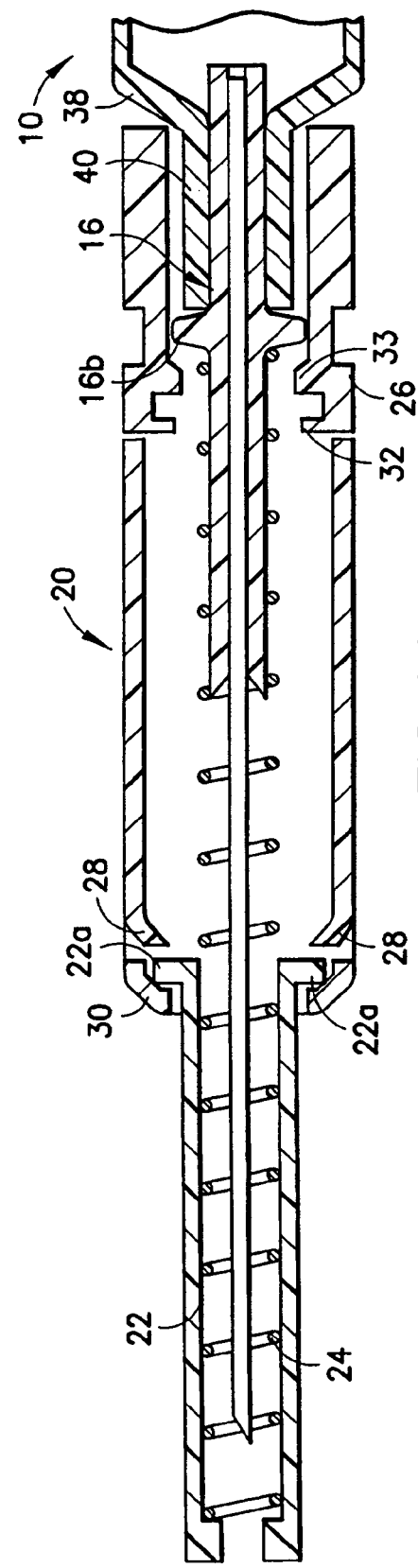
FIG. 11 is an enlarged view of the shield system in the state shown in FIG. 10.

Prior to use, the needle shield 27 is removed from the medical device 1 exposing the needle cannula 18 as shown in FIG. 7. The forward tip 19 of the needle cannula 18 is inserted into a patient for the delivery of the medicament. Delivery of the medicament is accomplished by application of a medicament delivery pressure to the thumb pad 15 causing the plunger rod 12 and stopper 14 to move into the barrel 10 and within the reservoir 13, thereby urging the medicament in the barrel 10 through the needle cannula 18. When the entire dosage of medicament has been delivered, the plunger rod 12 is almost fully inserted into the barrel 10 and the stopper 14 rests against the end of the needle pusher 16. To activate the shield system, the user applies additional pressure to the thumb pad 15 to urge the plunger rod 12 further into the barrel. This can occur while the needle cannula 18 is in the patient, or after it is removed from the patient. As the plunger rod 12 is pushed to its fully inserted position, the needle pusher 16 is urged out of the barrel to the position shown in FIGS. 8 and 9. As the needle pusher 16 is moved out of the barrel, any remaining medicament in the barrel is directed through slot 18a (see FIG. 3) into the needle cannula 18. In the position shown in FIGS. 8 and 9, the gasket 16b on the needle pusher 16 moves against shoulder 33 which urges flexible arms 26 apart from each other. This also moves retaining members 32 apart from each other, thereby releasing flange 22a from channel 31. Accordingly, and once the needle cannula 18 is no longer obstructed, e.g. the needle is removed from the patient, the second shield 22 can then be urged forward over the end of the needle cannula 18 by the urging member 24 to the position shown in FIGS. 10 and 11.

The second shield 22 is prevented from being ejected out of, or detaching from, the first shield 20 by a lip 30 formed at the front end of the first shield 20 which engages flange 22a. Furthermore, additional flexible arms 28 are arranged just behind the lip 30 and function as a one-way guide for allowing the flange 22a of the second shield to pass as the second shield 22 is moved over the needle cannula 18, and for preventing the second shield 22 from moving back into the first shield 20. The medical device 1 may then be safely handled without inadvertent stabbing or sticking of the user from the now-used and contaminated needle cannula 18.

Figure 14:
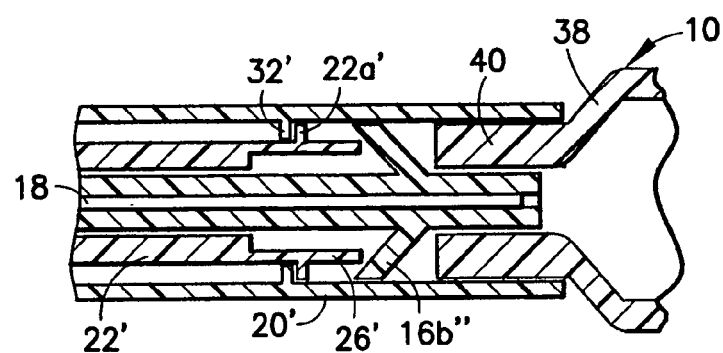
FIG. 14 is an enlarged cross-sectional view of a further embodiment of the shield system according to the present invention.

In an alternative embodiment shown in FIG. 14, the flexible arms 26' are arranged on the second shield 22' and tabs 22a' are arranged on the flexible arms 26' which interact with a flange 32' on the first shield 20' to retain the second shield 22' in the first shield 20'. The flange 16b" is angled toward a forward direction of motion of the second shield 22'. As the needle pusher 16 is moved via interaction with the plunger rod 12, flange 16b" interacts with arms 26' and urges them radially inward to clear flange 32' which releases the second shield 22' and allows it to move forward under the urgency of the urging member 24 (not shown in FIG. 14). Once the second shield 22' covers the needle cannula tip 19, the second shield 22' may be held in that position by a lip and a flange similar to the lip 30 and retainer 28 shown in FIG. 6. In this embodiment, the retainer 28 may comprise an annular member.

Figure 15:
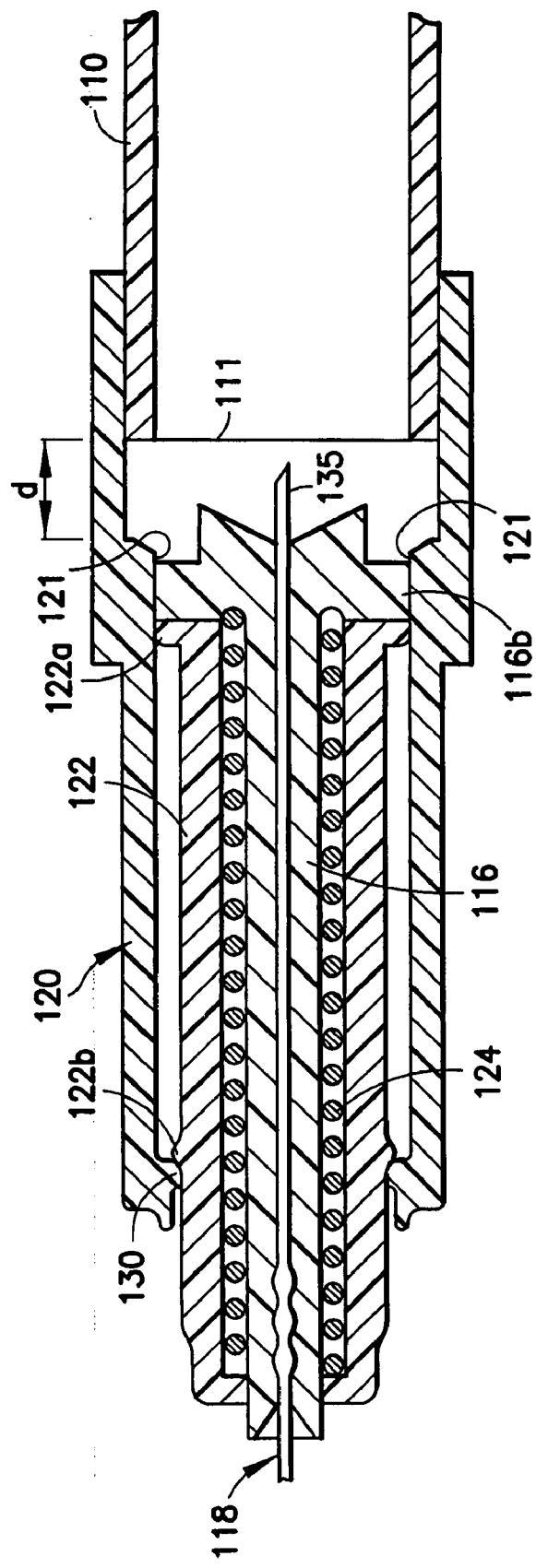
FIG. 15 is an enlarged cross-sectional view of another embodiment of the shield system according to the present invention.

In another embodiment shown in FIG. 15, the shield system 3 of a medical device 1 in accordance with the present invention includes an add-on assembly which may be provided to the user already attached to the syringe barrel 110 or may be provided as a separate component which is attached to the barrel 110 at the user end prior to use. The add-on assembly includes a first shield 120 that is slidably mounted to the front of a syringe barrel 110 and movable from a first position wherein a spike 135 is isolated from the reservoir as shown in FIG. 15, to a second position wherein the spike 135 is in communication with the reservoir. In this embodiment, the syringe barrel 110 is prefilled and incorporates a membrane such as a foil seal 111 at the end thereof or some other type of sealing membrane. In this way the syringe barrel 110 is stored with the medicament sealed therein until the time of use. To use the embodiment of FIG. 15, an activation step is performed so that the hollow spike 135 on the needle pusher 116 breaks through the foil seal 111.

FIG. 15 shows the first position of the barrel 110 before the spike 135 has broken the seal but before the barrel is fully coupled to the first shield 120. The first shield 120 can then be further inserted toward barrel 110 by a distance d to the second position i.e. to the fully coupled state. This embodiment operates similarly to the previous embodiments in that the plunger rod (not shown in FIG. 15) urges the needle pusher 116 forward relative to the first shield 120 by contacting the pusher hub region 116b to release a retaining device. In FIG. 15, the urging member 124 is arranged between the pusher hub region 116b and a second shield 122. The pusher hub region 116b is prevented from moving rearward by projection 121 which may be a rim or discrete projections. The second shield 122 is prevented from moving forward by the interaction between an annular bump 122b on the outer surface of the second shield, and a lip 130 of the first shield 120. As the needle pusher 116 is moved forward by the plunger rod, the second shield 122 is moved with the needle pusher 116 until the annular bump 122b passes the lip 130. At that point the urging member 124 urges the second shield 122 over the needle until the flange 122a of the second shield rests against the lip 130. This embodiment also includes a lock for holding the second shield 122 in the safe position, such as the flexible arms 28 shown in FIGS. 6 and 11. Of course, if the barrel 110 is not prefilled, the requirement for the spike 135 is obviated.

Figure 16:
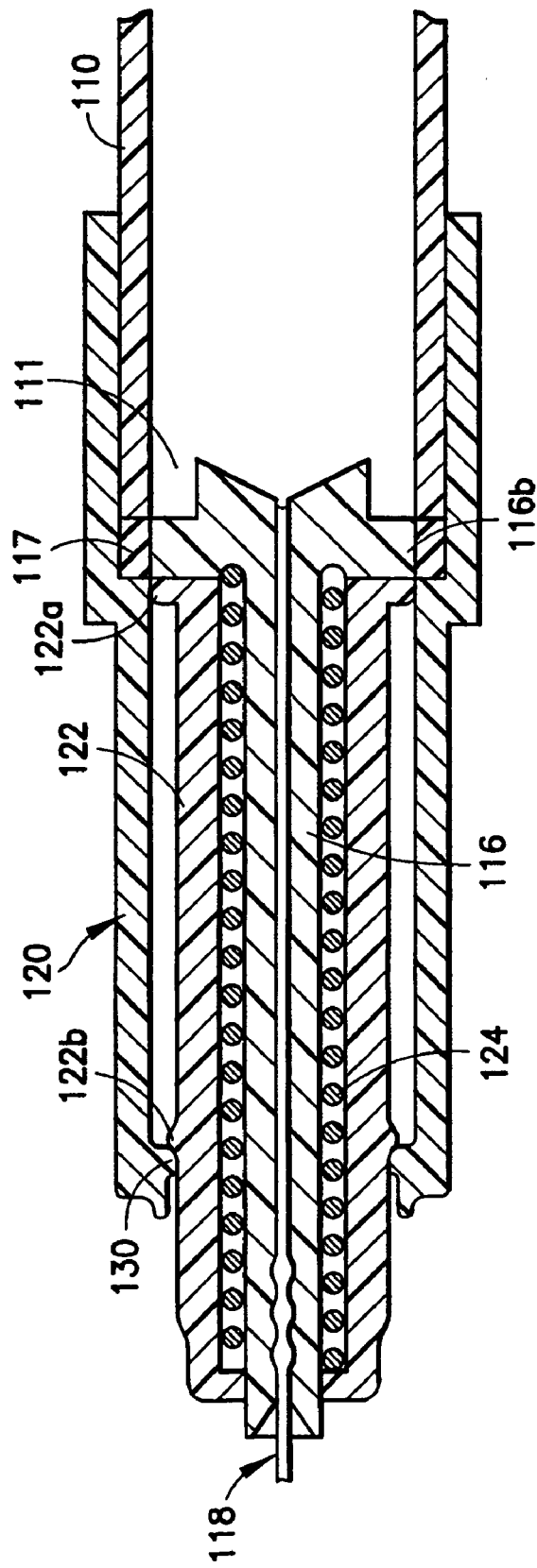
FIG. 16 is an enlarged cross-sectional view of yet another embodiment of the shield system according to the present invention.

FIG. 16 shows an alternative embodiment in which a seal 117 is arranged between the hub 116b of the needle pusher 116 and the first shield 120 for creating a seal between the barrel 110, the first shield 120 and the needle pusher 116. Operation of the embodiment shown in FIG. 16 is similar to that of FIG. 15. In both embodiments of FIGS. 15 and 16, a needle shield such as the needle shield 27 shown in FIG. 2 or needle shield 27' shown in FIG. 12 may be used for protecting the needle 118 prior to use.

Figure 11A:
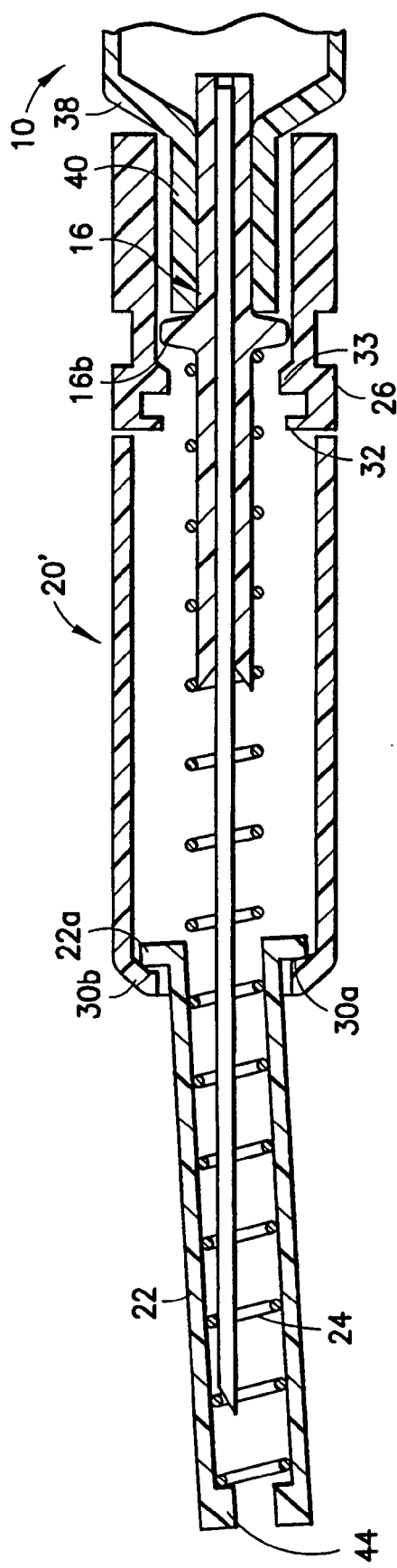
FIG. 11a is an enlarged cross-sectional view of alternative embodiment of a shield system according to the present invention.

FIG. 11a shows another alternative embodiment in which the lip 30' comprises first and second sections 30a, 30b that are axially offset from each other. When the second shield 22 is pushed into the activated position, the flange 22a first contacts the first section 30a which causes the second shield to pivot about the initial point of contact at section 30a until another part of the flange 22a rests on the second section 30b (or until the shield 22 contacts the needle cannula), as shown in FIG. 11a. In this position, the second shield 22 is askew relative to the needle cannula 18 and the needle cannula is not aligned with the hole in the wall 44 through which it was formerly inserted. This configuration prevents inadvertent sticks because when the second shield 22 is pressed into the first shield 20, the tip of the needle cannula 19 is not aligned with the hole in the wall 44 but, instead, contacts the wall 44 to maintain the needle tip within the second shield.

A description of an exemplary usage of the medical device 1 of the present invention will now be provided. It should be understood by a person of ordinary skill in the art that the following description is provided as an illustrative and non-limiting example. The health care professional receives the inventive medical device 1 prefilled with a desired single dosage of a medicament. Immediately prior to use, the needle shield 27 is removed and the needle cannula 18 and forward tip 19 are exposed. The health care professional pierces the patient's skin with the forward tip 19 of the needle cannula 18 and depresses the thumb pad 15 to cause the plunger rod 12 and stopper 14 to move within the reservoir 13. As the plunger rod 12 and stopper 14 are caused to move into the reservoir, the medicament is caused to be expelled from the reservoir, through the needle cannula 18, and into the patient. When the medicament is completely expelled from the reservoir (i.e., the dose has been completely administered), additional pressure will then be applied to the thumb pad 15 (with or without the needle cannula 18 removed from the patient), to urge the plunger rod further into the barrel. This further movement causes the needle pusher 16 to release flange 22a from the channel 31 whereby the second shield 22 will then be deployed by the urging member 24 to a position covering the needle cannula tip 19. Once so-deployed, the lip 30 formed at the front end of the first shield 20 engages flange 22a of the second shield to maintain coupling between the first and second shields. The covering of the needle cannula tip 19 by the second shield prevents undesired and inadvertent exposure of the health care professional to the contaminated tip 19. The used medical device 1 may then be disposed of in a suitable sharps disposal container.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical device for delivering a medicament to a patient, comprising:
   a syringe assembly comprising:
      a barrel with a forward end and a rear end and defining a reservoir within which the medicament may be contained;
      a needle cannula having a forward tip and being coupled to said forward end of said barrel and being in fluid communication with said reservoir; and a plunger rod having a stopper arranged at one end of said plunger rod and disposed in said reservoir, said plunger rod having a thumb pad arranged at the other end thereof, said thumb pad being operable for receiving medicament delivery pressure for causing said stopper to move within said reservoir to cause the medicament to be expelled from said reservoir; and a shield system comprising:
a first shield coupled to said forward end of said barrel;
a second shield movable from a first position to a second position;
an urging member urging said second shield toward said second position;
a retaining device for holding said second shield in said first position; and
a release mechanism for releasing said retaining device upon insertion of said stopper in said barrel to a release mechanism deployment position;
wherein said second shield comprises a flange at an end of said second shield, said retaining device acting on said flange for holding said second shield in said first position; and
wherein said forward tip of said needle cannula is at least partially exposed for allowing delivery of the medicament to the patient when said second shield is in said first position and said forward tip of said needle cannula tip is covered by said second shield when said second shield is in said second position.

2. The medical device of claim 1, wherein said shield system is arranged on said syringe assembly such that said shield system is positioned in front of said reservoir so as not to visually obstruct said reservoir and the medicament held therein.

3. The medical device of claim 1, wherein said second shield is located in said first shield when said second shield is in said first position.

4. The medical device of claim 3, wherein said retaining device comprises a flexible arm having a retaining member for interaction with said flange.

5. The medical device of claim 4, wherein said release mechanism comprises a tubular element arranged on said needle cannula and sealingly inserted with said needle cannula in an opening at said front of said barrel.

6. The medical device of claim 5, wherein said tubular element extends into said barrel such that said stopper contacts said tubular element at a contact position before said stopper is fully inserted in said barrel, said tubular element being movable by said stopper as said stopper moves from said contact position to the release mechanism deployment position, said tubular element forcing said flexible arm of said retaining device radially outward when said tubular element is moved by said stopper.

7. The medical device of claim 6, wherein said urging member is arranged between said tubular element and said second shield.

8. The medical device of claim 6, wherein said tubular element comprises a tubular portion and a flange portion arranged between two longitudinal ends of said tubular portion, said tubular portion being molded from a rigid material for supporting said needle cannula and said flange portion being molded from a flexible material having a flexibility sufficient to provide a seal at the forward end of said barrel.

9. The medical device of claim 8, wherein said flange portion interacts with said retaining device to release said second shield.

10. The medical device of claim 8, wherein said urging member is arranged between said flange portion of said tubular element and said second shield.

11. The medical device of claim 1, wherein a front end of said first shield comprises a lip for retaining the flange of said second shield at said second position when said second shield is moved to said second position.

12. The medical device of claim 11, further comprising a locking device for locking said second shield in said second position.

13. The shield system of claim 11, wherein said lip includes first and second sections axially offset from each other for engaging said flange of said second shield when said second shield is moved to said second position for causing misalignment of said second shield with respect to a longitudinal axis of said needle cannula.

14. The medical device of claim 12, wherein said locking device allows said flange to pass said locking device as said second shield moves toward said second position and prevents said second shield from moving back toward said first position from said second position.

15. The medical device of claim 3, wherein said second shield comprises an annular bump between first and second ends of said second shield, wherein said retaining device comprises a lip arranged at a front end of said first shield interacting with said annular bump.

16. The medical device of claim 15, wherein said release mechanism comprises a tubular element arranged on said needle cannula and comprising a hub portion facing said barrel, said stopper contacting said hub portion at a contact position before said stopper is fully inserted in said barrel, said tubular element and hub being longitudinally movable by said stopper when said stopper is moved from said contact position to said fully inserted position in said barrel, said tubular element moving said second shield such that said annular bump passes said lip to release said second shield when said stopper is fully inserted.

17. The medical device of claim 1, wherein said barrel comprises a cylindrical barrel portion, a front cylindrical portion having a different diameter than said cylindrical barrel portion, and a transition portion between said front cylindrical portion and said cylindrical barrel portion.

18. The medical device of claim 17, wherein said release mechanism comprises a tubular element arranged on said needle cannula and sealingly inserted with said needle cannula in an opening defined by said front cylindrical portion.

19. The medical device of claim 18, wherein said first shield is connected on an outer surface of said front cylindrical portion.

20. The medical device of claim 19, wherein said cylindrical barrel portion is made from a plastic material.

21. The medical device of claim 19, wherein said cylindrical barrel portion is made from a glass material.

22. The medical device of claim 19, wherein said cylindrical barrel portion is made from a glass material and said front cylindrical portion is made from a plastic material.

23. The medical device of claim 19, wherein said first shield is connected to said outer surface of said front cylindrical portion by one of a snap-fit connection, an adhesive, threading, welding, and a heat stake.

24. A combination comprising a syringe assembly for delivery of a medicament to a patient, and a shield system for use with said syringe assembly;
wherein said syringe assembly comprises a barrel having a forward end and a rear end and defining a reservoir within which the medicament may be contained, a needle cannula having a forward tip and coupled to said forward end of said barrel, said needle cannula being in fluid communication with said reservoir, and a plunger rod having a stopper arranged at one end of said plunger rod and disposed in said reservoir, said plunger rod having a thumb pad arranged at the other end thereof, said thumb pad being operable for receiving medicament delivery pressure for causing said stopper to move within said reservoir to cause the medicament to be expelled from said reservoir;

wherein said shield system comprises a first shield coupled to said forward end of said barrel, a second shield movable from a first position to a second position, an urging member urging said second shield toward said second position, a retaining device for holding said second shield in said first position, and a release mechanism for releasing said retaining device upon insertion of said stopper in said barrel to a release mechanism deployment position;

wherein said second shield comprises a flange at an end of said second shield, said retaining device acting on said flange for holding said second shield in said first position; and wherein said needle cannula is at least partially exposed for allowing delivery of the medicament to the patient when said second shield is in said first position and said forward tip of said needle cannula tip is covered by said second shield when said second shield is in said second position.

25. The combination of claim 24, wherein said barrel comprises a cylindrical barrel portion, a front cylindrical portion having a different diameter than said cylindrical barrel portion, and a transition portion between said front cylindrical portion and said cylindrical barrel portion.

26. The combination of claim 25, wherein said release mechanism comprises a tubular element arranged on said needle cannula and sealingly inserted with said needle cannula in an opening defined by said front cylindrical portion.

27. The combination of claim 26, wherein said first shield is connected to an outer surface of said front cylindrical portion.

28. The combination of claim 27, wherein said cylindrical barrel portion is made from a plastic material.

29. The combination of claim 27, wherein said cylindrical barrel portion is made from a glass material.

30. The combination of claim 27, wherein said cylindrical barrel portion is made from a glass material and said front cylindrical portion is made from a plastic material.

31. A shield system for connection to a syringe barrel for preventing inadvertent needle sticks after use of the syringe, the shield system comprising a first shield having a first end coupled to a front end of the syringe barrel, a second shield movable from a first position to a second position, an urging member urging said second shield toward said second position, a retaining device for holding said second shield in said first position, and a release mechanism for releasing said retaining device upon insertion of a syringe stopper into the syringe barrel to a release mechanism deployment position for allowing said urging member to move said second shield to said second position to cover a tip of a needle cannula connected to said forward end of the syringe barrel, wherein said second shield comprises a flange at an end of said second shield, said retaining device acting on said flange for holding said second shield in said first position.

32. The shield system of claim 31, wherein said second shield is located in said first shield when said second shield is in said first position.

33. The shield system of claim 30, wherein said retaining device comprises a flexible arm having a retaining element for interaction with said flange.

34. The shield system of claim 33, wherein said release mechanism comprises a tubular element arranged on the needle cannula and sealingly inserted with said needle cannula in an opening at the front end of the syringe barrel.

35. The shield system of claim 34, wherein said urging member is arranged between said tubular element and said second shield.

36. The shield system of claim 31, wherein a front end of said first shield comprises a lip for retaining said flange of said second shield at said second position when said second shield is moved to said second position.

37. The shield system of claim 36, further comprising a locking device for locking said second shield in said second position.

38. The shield system of claim 37, wherein said locking device allows said flange to pass said locking device as said second shield moves toward said second position and prevents said second shield from moving back toward said first position from said second position.

39. The shield system of claim 32, wherein said second shield comprises an annular bump between first and second ends of said second shield, wherein said retaining device comprises a lip arranged at a front end of said first shield interacting with said annular bump.

40. The shield system of claim 36, wherein said lip includes first and second sections axially offset from each other for engaging said flange of said second shield when said second shield is moved to said second position for causing misalignment of said second shield with respect to a longitudinal axis of said needle cannula.

41. A medical device for delivering a medicament to a patient, comprising:

a syringe assembly comprising:
    a barrel with a forward end and a rear end and defining a reservoir within which the medicament may be contained;
    a needle cannula having a forward tip and being coupled to said forward end of said barrel and being in fluid communication with said reservoir; and
    a plunger rod having a stopper arranged at one end of said plunger rod and disposed in said reservoir, said plunger rod having a thumb pad arranged at the other end thereof, said thumb pad being operable for receiving medicament delivery pressure for causing said stopper to move within said reservoir to cause the medicament to be expelled from said reservoir; and a shield system comprising:
    a first shield coupled to said forward end of said barrel;
    a second shield movable from a first position to a second position;
    means for urging said second shield toward said second position;
    means for retaining said second shield in said first position; and
    means for releasing said retaining means upon insertion of said stopper in said barrel to a deployment position;

wherein said second shield comprises a flange at an end of said second shield, said retaining means acting on said flange for holding said second shield in said first position;

wherein said forward tip of said needle cannula is at least partially exposed for allowing delivery of the medicament to the patient when said second shield is in said first position and said forward tip of said needle cannula tip is covered by said second shield when said second shield is in said second position.

* * * * *